United States Patent [19]
Michelson

[11] Patent Number: 5,195,526
[45] Date of Patent: Mar. 23, 1993

[54] SPINAL MARKER NEEDLE

[76] Inventor: Gary K. Michelson, 438 Sherman Canal, Veince, Calif. 90291

[21] Appl. No.: 633,999

[22] Filed: Dec. 26, 1990

Related U.S. Application Data

[63] Continuation of Ser. No. 421,963, Oct. 16, 1989, abandoned, which is a continuation-in-part of Ser. No. 167,167, Mar. 11, 1988, abandoned.

[51] Int. Cl.$^5$ .................. A61M 5/02; A61M 5/00
[52] U.S. Cl. .................... 128/654; 604/117; 604/116; 604/182; 604/201; 604/232; 604/272
[58] Field of Search ............. 128/DIG. 26, 654, 655, 128/656; 604/38, 48, 51, 93, 100, 116-117, 174, 180-182, 244, 264, 132, 232, 234, 272, 222, 218, 200-202, 164, 49; 606/116, 172, 185; 378/162-164, 205

[56] References Cited

U.S. PATENT DOCUMENTS

| | | | |
|---|---|---|---|
| 2,590,895 | 4/1952 | Scarpellino | 128/654 |
| 4,197,846 | 4/1986 | Bucalo | 604/51 |
| 4,774,948 | 10/1988 | Markham | 604/164 |
| 4,834,704 | 5/1989 | Reinicke | 604/51 |
| 4,940,458 | 7/1990 | Cohn | 604/51 |
| 4,985,019 | 1/1991 | Michelson | 604/180 |

OTHER PUBLICATIONS

Primary Examiner—Randall L. Green
Assistant Examiner—K. Reichle
Attorney, Agent, or Firm—Lewis Anten

[57] ABSTRACT

A radiographically opaque spinal marker needle having a lower portion consisting of a small bore hollow needle and an upper portion having a larger outside diameter. An intermediate penetration restriction member fixed to and surrounding the marker needle at a point proximate the junction of the upper portion and the lower portion limits the depth of penetration of the hollow needle into the patient or tissue, provides stability, and forms a large observable mass on an X-ray. In an alternative embodiment the larger upper bore portion is in the form of a syringe and includes a prefilled ampule of dye within the syringe for injection into the patient by a plunger assembly. The upper portion may be separable from the lower portion at a point above the pentration restriction member.

16 Claims, 4 Drawing Sheets

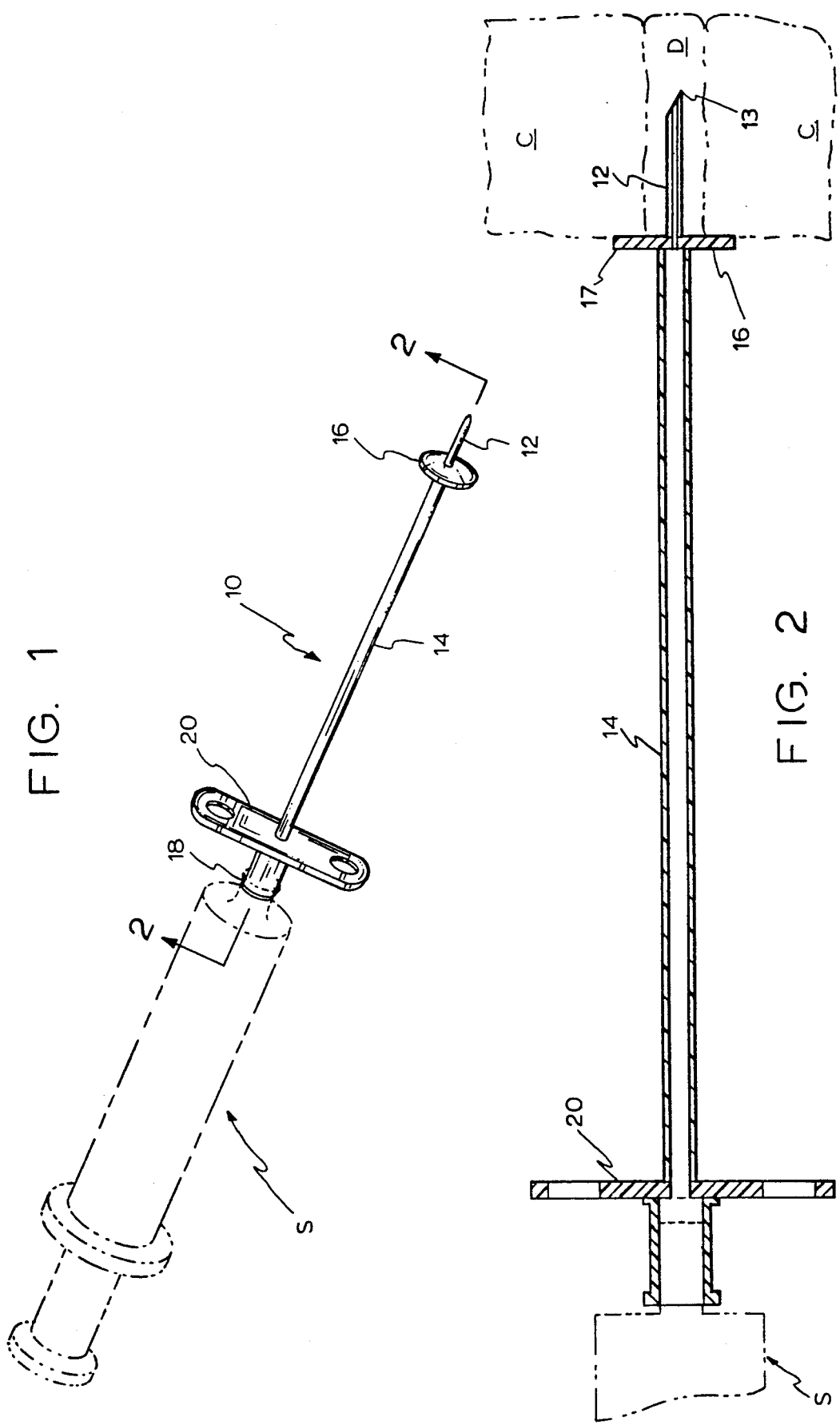

FIG. 3
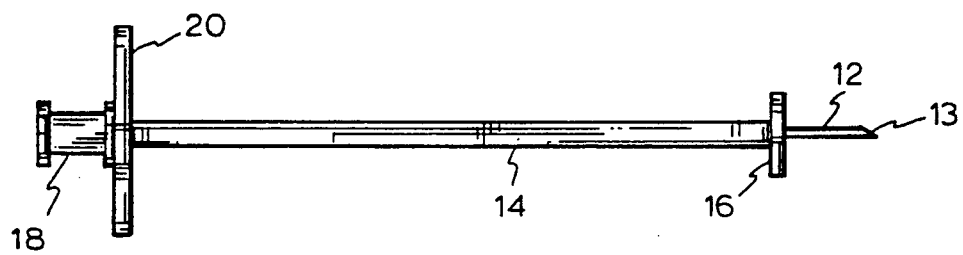
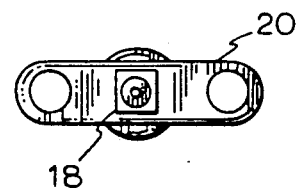
FIG. 5
FIG. 4
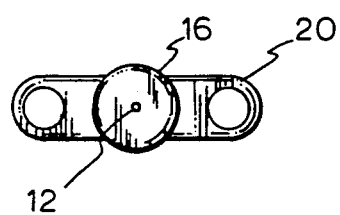
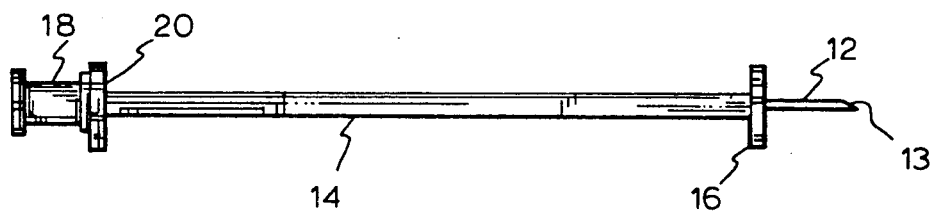
FIG. 5(a)

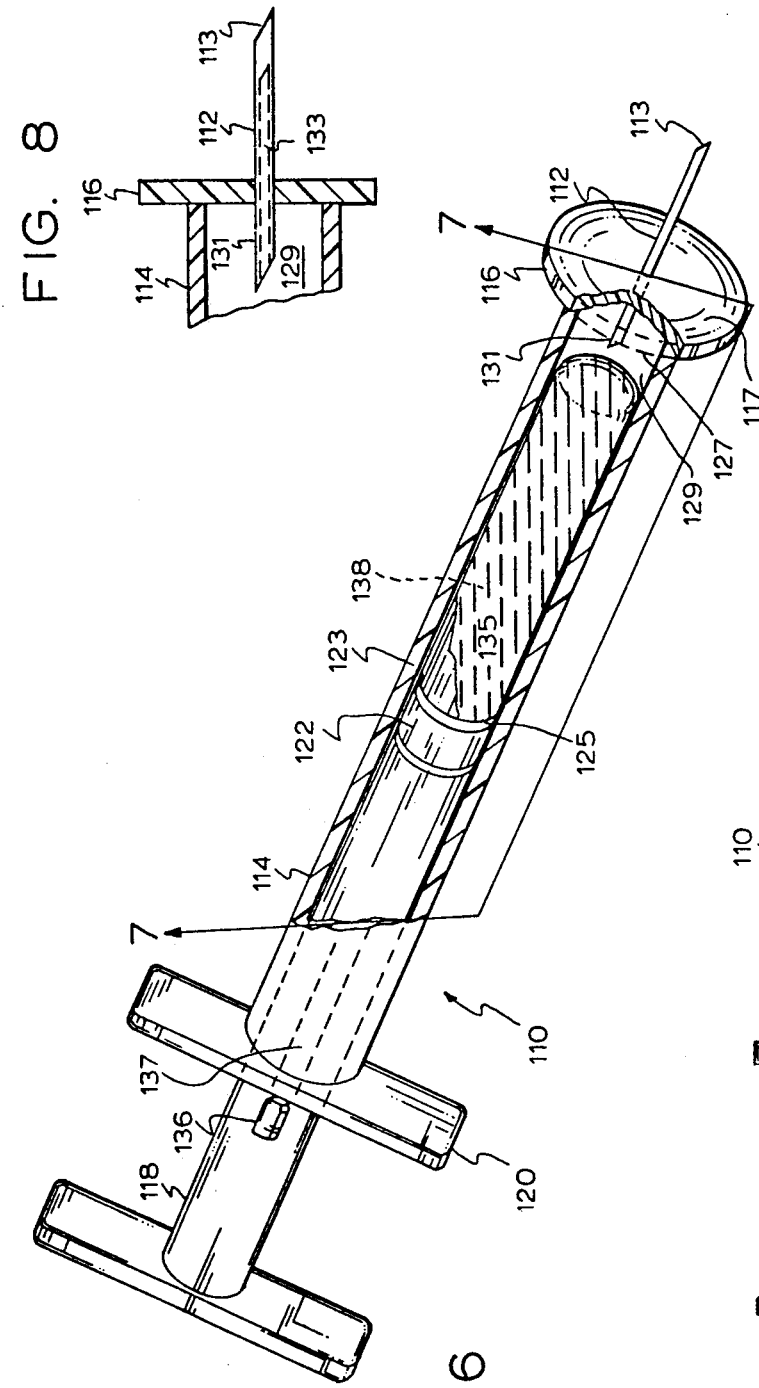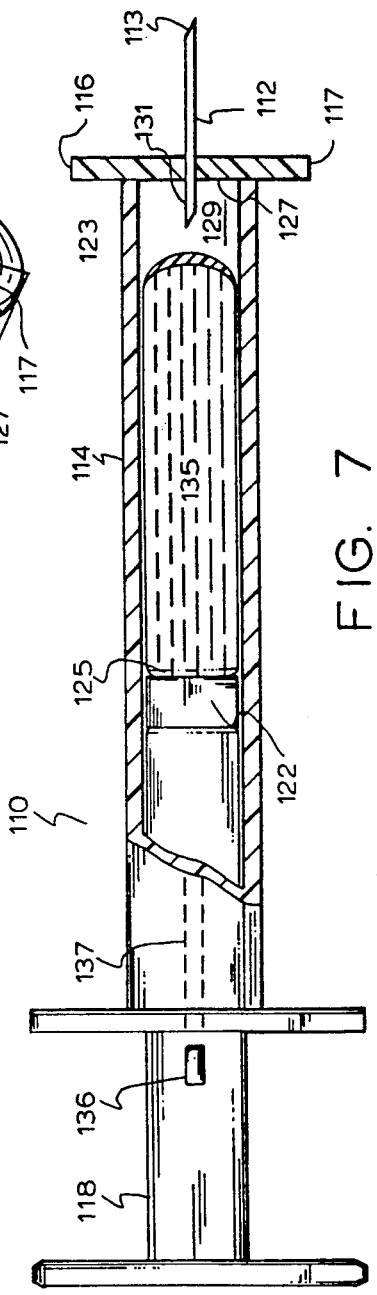

SPINAL MARKER NEEDLE

RELATED APPLICATIONS

This is a continuation of application Ser. No. 07/421,963 filed on Oct. 16, 1989, now abandoned that application is a continuation in part application of patent application Ser. No. 167,167 for SPINAL NEEDLE, filed Mar. 11, 1988 by Gary Karlin Michelson, M.D., now abandoned.

BACKGROUND OF THE INVENTION

When a surgeon performs a cervical discectomy, prior to cutting into the disc, since under most circumstances all discs look the same from the front, it is common practice for the surgeon to surgically expose the disc and then place a hollow radiographically opaque needle into the suspect disc and then X-ray the disc and needle to make sure the needle is in the proper disc. On hopes that the needle is going into the disc to be removed, however, errors frequently occur and the disc in which the needle is placed will turn out to be a perfectly healthy disc, and the disc desired to be removed will have been one either higher or lower. When the proper disc is located a dye is injected through the hollow marker needle into the disc.

Inasmuch as one is not assured prior to obtaining the radiograph that the marker needle is in the correct disc, it is desirable to use a marker needle of the smallest possible caliber so that in the event it should prove to be in the wrong disc, the disc itself will not have been harmed by the marker needle. Quite obviously, the placement of a large, thick, heavy needle through the casing of the disc and into its substance is harmful.

At the same time, while it is desirous for the reasons already discussed to use a marker needle of small caliber in entering the disc, it is necessary to use a marker needle of as heavy a caliber as possible so that it will show up clearly on the radiograph. This creates a conflict since presently available spinal marker needles maintain the same internal and external diameter from tip to end.

Another set of problems concerning the use of existing marker needles deals with the fact that the approach, for example to the cervical spine, is actually from a lateral aspect to a midline structure. Therefore, when one is working on the front of the cervical spine but approaching it laterally, it is possible to maintain the overlying structures out of the way only by retracting them with either hand held or self-retaining retractors.

The retractors cannot be left in place for the radiograph as they are metal, and they would obscure the marker needle itself. Therefore, when the retractors are removed there is a strong tendency for the midline cervical structures to want to return to their normal location, thereby dislodging the marker needle from the disc. Such a dislodged needle is then useless as a marker and threatens with penetration the vital structures of the neck.

The marker needles that are used for this purpose at the present time typically tend to be about 8 centimeter long spinal needles, and these marker needles have no real capability or special innovation to resist such dislodgement. There is a tendency on the part of the surgeon to try to place the needle as deeply into the disc as possible to stabilize it. However, the surgeon is always fearful of over penetrating the disc and pithing the spinal cord, possibly paralyzing the patient. Thus, there are conflicting desires, that is, the desire to place the marker needle deeply within the disc to provide stability to the needle, and the desire to avoid over penetration of the disc and pithing of the spinal cord. The difference between a good deep placement and pithing the spinal cord may not be more than several millimeters.

At the present time, most surgeons clamp the spinal marker needle with a hemostat or bent mosquito-type hemostat approximately a centimeter from the tip, thereby attempting to provide for approximately one centimeter of penetration of the needle tip, avoiding over penetration. However, the placement of the clamp about the marker needle contributes to the problem of the marker needle dislodging, for the clamp itself has both mass and occupies space. Therefore, when the muscles and the midline cervical structures fall back into place, they tend to pull against the clamp, only complicating the problem of keeping the marker needle upright. Furthermore, as these clamps are not truly designed for the purposes which they are being used, there is the danger of the clamp popping off of the marker needle, and the marker needle then being pushed into the spinal cord.

The next step in the process of obtaining the radiograph is that an X-ray machine must be brought in and placed close to the patient's neck and the operating area. Since the operating area is sterile, and the X-ray machine is not, a large drape or sheet is placed over the operative field. As the marker needle is now the highest object on the field, the sheet frequently comes to rest onto the spinal marker needle and presses against it. This presents a potential danger to the patient, as the marker needle can over penetrate if the clamp should come off.

After the marker needle is utilized to locate the correct placement for the surgical incision or the appropriate disc, a dye (indigo carmine, functional or equivalent) is injected by a syringe into the disc, coloring the nucleus of the disc so that the physician can make sure that all of the pathological disc has been removed.

Typically, it is necessary for the operating room nurse to go to another location to obtain said dye, which is maintained in bulk, and the operating room nurse must then pour the dye into the syringe. The sterility of the marking dye is accordingly compromised.

Further, a second dye typically used in an operating room is methylene blue dye, which is neurologically toxic. These two agents are packed in similar appearing containers. A mix-up by the operating nurse between the two dyes could result in paralysis of the patient.

SUMMARY OF THE INVENTION

The present invention comprises a radiographically opaque marker needle having a lower portion consisting of a small bore needle and an upper portion having a larger outer diameter than the lower portion. A relatively large penetration restriction member, preferably in the form of a circular disc, surrounds the periphery of the marker needle proximate the junction between the lower portion needle and the upper portion assuring the ideal depth of insertion of the marker needle, providing for stabilization against dislodgement and providing a relatively large mass directly over the disc space. The upper portion of the marker needle is either in the form of a syringe (empty or preloaded with dye) or has a means for attachment to a conventional syringe.

In the embodiment of the present invention in which the upper portion is in the form of a syringe, an ampule of dye is maintained in the upper portion of the marker needle. A plunger fitted within the upper portion compresses an ampule of dye against an internal hollow needle which causes the rupture of the ampule, permitting the plunger of the syringe to eject the dye through the hollow needle into the disc of the patient.

OBJECTS OF THE PRESENT INVENTION

It is the object of the present invention to provide an improved marker needle.

It is a further object of the present invention to provide an improved marker needle that is easier to locate on an X-ray.

It is another object of the present invention to provide an improved marker needle that is safer to use.

It is a yet another object of the present invention to provide an improved marker needle that is more stable.

It is an object of the present invention to provide an improved marker needle which is pre-filled with dye.

It is another object of the present invention to provide an improved marker needle which is more economical.

It is another object of the present invention to provide an improved marker needle which is quicker and more reliable to use than previously available marker needles.

These and other objects of the present invention will be evident from a review of the specification and the accompanying drawings.

BRIEF DESCRIPTION OF THE DRAWINGS

FIG. 1 is a perspective view of the first embodiment of the present invention, with an accompanying separate syringe used with the marker shown in dotted lines.

FIG. 2 is a side sectional view of the present invention, taken along lines 2—2 of FIG. 1

FIG. 3 is the right side view of the marker needle of FIG. 1.

FIG. 4 is a top view of the marker needle of FIG. 1.

FIG. 5 is a bottom view of the marker needle of FIG. 1.

FIG. 5a is a right side view of a lumbar surgery marker needle.

FIG. 6 is a partial sectional perspective view of the combination marking needle and dye dispenser.

FIG. 7 is a partial sectional side view of the device of FIG. 6 taken along lines 7—7 of FIG. 6.

FIG. 8 is an alternative embodiment of the device of FIG. 6 having an increased diameter needle for use with the lumbar spine.

DETAILED DESCRIPTION OF THE DRAWINGS

Figure 10:
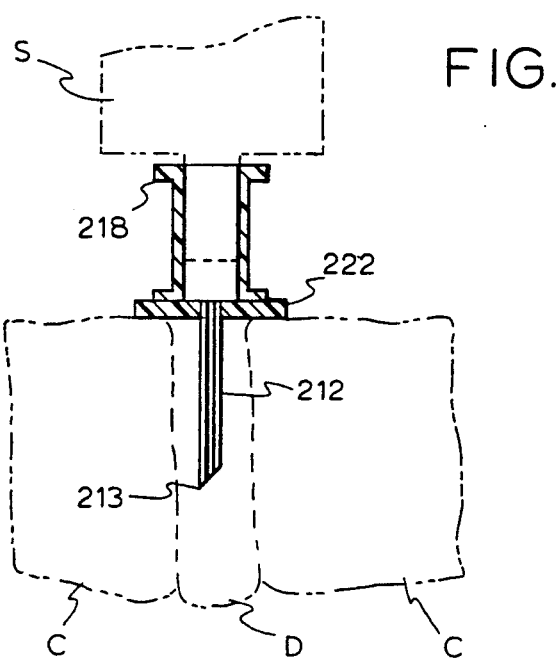
FIG. 10 is an alternative embodiment of FIG. 9, showing the upper portion attached to a syringe.

Referring to FIGS. 1-5, the basic marker needle 10 is shown having a hollow lower needle portion 12 consisting of a small bore needle terminating in a sharp end 13 and a hollow upper portion 14. A penetration restriction member 16, preferably in the form of a disc is mounted peripherally about the marker needle 10 at the juncture of the upper portion 14 and lower portion 12.

A syringe attachment means 18 is associated with the upper portion 14 of the marker needle 10 for attachment to the syringe. In the preferred embodiment, the attaching means comprises a Leur lock. Perpendicular projections 20 extend from the upper portion 14 proximate the syringe attachment means to facilitate the operation of the syringe S.

The lower needle portion 12 has an internal bore of about a number 23 gauge needle, an external diameter of a number 23 gauge needle and a longitudinal dimension of about 1 centimeter from the penetration restriction member 16. The upper portion 14 of the marking needle 10 is extremely heavy walled, having an inner and an outside diameter comparable to a number 14 gauge needle, and is approximately 7.5 centimeters long.

The penetration restriction member 16 is in the form of a round disc, about the size of a dime, having an outer diameter of about 17 millimeters and is about 2 millimeters thick. The disc is flat on at least its bottom surface. The diameter of the penetration restriction member 16 disc is substantially larger than the diameter of the lower portion 12 of the marker needle, preferrably more than five times the diameter of the lower portion 12. However, other shapes and sizes for the penetration restriction member discs, such as those comparable to a nickel and other shapes other than a circular disc configuration may be used. The peripheral edge 17 of the penetration restriction number 16 serves to stabilize the needle and prevent dislodgement of the marker needle during use.

For use in lumbar surgery the lower portion 12, shown in FIG. 5a, would be of a larger bore than that of FIG. 1 and thick walled on the order of a heavy 14–18 gauge needle, in order to penetrate into bone if needed, without bending or breaking.

Typically the lumbar embodiment would be inserted with the patient on the operating table but prior to making the incision. The penetrating lower portion 12 is sufficiently short to allow penetration into the spinous process or inter spinous ligament without danger of over penetration into the spinal canal and dural sac. As it is, such placement requires considerable force. The presence of the penetration restriction member avoids over penetration which is a significant advance as the spinous process is somewhat nosecone shaped and it would otherwise be easy to slip off with the needle and result in over penetration and cause neurological injury within the spinal canal below.

While the entire marker needle 10 may be made of highly radio-opaque material such as metal, only portions may be radiographically opaque. It may be desirable to make the upper portion of the marker needle of a light weight material, such as plastic. In such a case, the upper portion 14 would be injection molded in one piece and then connected to the lower portion 12 of the marker needle 10 above the penetration restriction member 16 by any number of conventional means. Further, if the penetration restriction member is radiographically opaque it would be sufficient alone to locate the desired disc. In an alternative embodiment, only the upper portion may be radiographically opaque, the upper portion serving as an arrow to show the desired disc to be removed.

The one centimeter length of the lower portion 12 for placement into the disc D between two vertebrae C of the patient assures deep seating of the marker needle 10, and at the same time, prevents inadvertent over penetration. The penetration restriction member 16 placed on the outer periphery of the marker needle 10, where the upper 14 and lower portion 12 meet, assures stability against migration or tilting of the marker needle 10. The penetration restriction member permits the marker needle 10 to be maintained in a substantially perpendicular orientation relative to the patient. The penetration restriction member 16 is positioned in the disc D and is extremely radiopaque when visualized in a lateral projection of an X-ray.

In the preferred embodiment, the penetration restriction member 16 is formed integrally with the lower and upper portions. However, the penetration restriction member may be movable in relationship to upper and lower portions by means of a threaded connection bayonet attachment means or other means that would prevent its movement during insertion into the disc.

Once the proper pathologic disc has been located, the surgeon attaches the syringe to the syringe connecting means of the marker needle and injects the dye into the disc for the purpose of staining the disc so as to allow the doctor to search out and remove small fragments of disc which may otherwise be hidden.

Referring to FIGS. 6–7, an alternative embodiment of the invention is shown in which the upper portion is in the form of a syringe containing a prefilled ampule of dye 138. The hollow marker needle 110 is shown having a hollow lower needle portion 112 terminating in a sharp end 113 and a hollow upper portion 114. A penetration restriction member 116 is mounted peripherally about the juncture of the upper portion 114 and lower portion 112.

A plunger 118 is fitted within the upper portion 114 of the marker needle 110. Finger grasping projections 120 extend perpendicularly from the upper portion 114. The plunger 118 has a lower rubber seal portion 122 for creating an air tight sliding relationship with the inner wall of the bore 123 of the upper portion 114.

The upper portion 114 of the marker needle 110 resembles a conventional 1 cc syringe. It is approximately 7.5 centimeters long. The space below the lower surface 125 of the rubber member 122 of the plunger 118 and the bottom surface 127 of the bore 123 of the upper member 114 forms a chamber 129. Extending upwardly from the bottom surface 127 is a projecting needle 131 which is hollow and axially aligned with the center bore 133 of the lower portion 112.

Fitted within the chamber 129 is an ampule 135 containing marking dye 138. While the predetermined amount of dye 138 is contained in a flexible ampule, other types of ampules, including rigid prefilled ampules, may also be used with an appropriate ejection system. The amount of dye 138 contained within the ampule is approximately 0.2–1.0 cubic centimeters. In the preferred embodiment, ampule 135 consists of polyethylene bag of thin consistency so that upon depression of the plunger 118 the ampule 135 is pressed against an upraised hollow needle 131 within the upper portion 114 and in fluid connection with the hollow lower needle portion 112 which ruptures the ampule, ejecting the dye 138 into the chamber 129 where it is then forced by action of plunger 118 through the lower member 112 and into the patient. While a plunger assembly is used for forcing the dye 138 into the patient, other means of forcing the dye 138 into the patient may be employed. or example, a compression member may be fitted on the side of the upper portion, movable to compress the ampule.

Projection 136 on the outside of the plunger 118 prevents depression of the plunger 118 unless the plunger is rotated so as to align the projection 136 with a corresponding slot 137 on the wall of the upper portion 114. This prevents accidental depression of the plunger 18 and subsequent ejection of the dye 138. Also, other means to prevent accidental ejection of the dye 138 may be used. The bottom portion of the ampule may be thickened or an intervening spacer may be used so as to prevent accidental puncturing of the ampule by needle 131.

Figure 9:
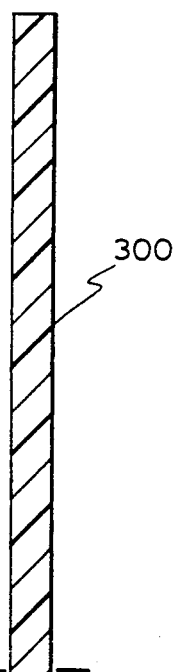
FIG. 9 is an alternative embodiment of the present invention in which the upper portion is separately shown attached to a removable rod.

A further embodiment is shown in FIGS. 9 and 10. The hollow lower needle portion 212 depends from disc 222. Needle 212 terminates in a sharp end 213. The needle portion 212 extends into disc D of the patient between vertebrae C. The upper portion may initially be in the form of a solid rod 300, removably attached to an uprising portion 218 above the penetration restriction 222. The uprising portion 218 is dimensioned as to receive a syringe as well as the rod 300 shown in FIG. The rod 300 is either of such a size as to engage fictionally to the inside of the uprising portion 218 or is attachable by other means during the X-ray stage. After the proper disc is located, the rod 300 is removed and a syringe S is attached to the uprising portion 218 and dye is injected into the patient.

While the invention has been described with respect to the preferred embodiments, other variations may be devised which do not depart from the concept of the present invention.

What I claim is:

1. A marker needle comprising a hollow upper portion and a lower portion having a longitudinal axis, said upper portion and said lower portion joining at a juncture, the lower portion comprising a hollow needle about 1 centimeter long, said upper portion having a larger outside diameter than the outside diameter of said lower portion, and penetration restriction means for restricting the depth of penetration of said lower portion of said marker needle, said penetration restriction means being at least 1 centimeter in diameter and fixed to said marker needle proximate said juncture of said upper portion and said lower portion, said penetration restriction means comprising a member extending perpendicular to the longitudinal axis of said lower portion and being substantially larger in diameter than the outside diameter of said lower portion, at least a portion of said marker needle being radiographically opaque.

2. A marker needle comprising a hollow upper portion and a lower portion having a longitudinal axis, said upper portion and said lower portion joining at a juncture, the lower portion comprising a hollow needle about 1 centimeter long, said upper portion having a larger outside diameter than the outside diameter of said lower portion, and penetration restriction means for restricting the depth of penetration of said lower portion of said marker needle, said penetration restriction means is greater than 15 millimeters in diameter and fixed to said marker needle proximate said juncture of said upper portion and said lower portion, said penetration restriction means comprising a member extending perpendicular to the longitudinal axis of said lower portion and being substantially larger in diameter than the outside diameter of said lower portion, at least a portion of said marker needle being radiographically opaque.

3. A marker needle having a hollow lower needle segment and an upper tubular segment having a larger outside diameter than the outside diameter of said needle segment, said upper tubular segment and said lower needle segment joining at a juncture, said marker needle having an external penetration restriction means surrounding said juncture of said upper segment and said lower needle segment for restricting the penetration of said lower needle segment into the patient, said upper segment having an internal chamber for retaining marking dye, and marking dye within said chamber and a plunger movable within said upper tubular segment, said dye being ejected from the needle by movement of said plunger movable within said upper segment.

4. The apparatus of claim 3 in which said marking dye is contained within an ampule fitted within said chamber.

5. The apparatus of claim 4 in which said ampule comprises a flexible plastic container.

6. The apparatus of claim 4 in which said upper segment has an internal penetration means for penetrating said ampule.

7. The apparatus of claim 6 in which said penetration means comprises a hollow needle, said hollow needle being in fluid communication with said lower needle segment.

8. The apparatus of claim 6 wherein said internal penetration means further comprises longitudinal puncturing means for puncturing and forcing said dye into said lower needle segment.

9. A marker needle having a lower hollow needle segment and a tubular upper portion having a larger outside diameter than the outside diameter of said lower needle segment, said lower needle segment and said upper portion joining at a juncture, said marker needle having an external penetration restriction means proximate the juncture of said lower segment and said upper portion for restricting the penetration of said lower needle segment into the patient, said upper portion having a chamber for retaining a predetermined amount of dye, and dye within said chamber and ejection means movable within said upper portion for ejecting said dye from within said upper portion, said ejection means comprising a movable member.

10. The apparatus of claim 9 in which said dye is contained within an ampule fitted within said chamber.

11. The apparatus of claim 10 in which said ampule comprises a flexible polyethylene container.

12. The apparatus of claim 10 in which said upper portion has an internal penetration means for penetrating said ampule.

13. The apparatus of claim 12 in which said penetration means comprises a hollow needle.

14. The apparatus of claim 10 in which said ejection means comprises a compression means for compressing said ampule containing said predetermined amount of dye.

15. The apparatus of claim 9 in which said ejection means comprises a plunger assembly slidable within said chamber.

16. The apparatus of claim 9 including detent means movable between a first position and a second position for preventing movement of said ejection means.

* * * * *